United States Patent [19]

Doyle et al.

[11] Patent Number: 5,168,063
[45] Date of Patent: Dec. 1, 1992

[54] MONOCLONAL ANTIBODY TO ENTEROHEMORRHAGIC *ESCHERICHIA COLI* 0157:H7 AND 026:H11

[75] Inventors: Michael P. Doyle; Nisha Padhye, both of Madison, Wis.

[73] Assignee: Wisconsin Alumni Research Foundation, Madison, Wis.

[21] Appl. No.: 559,867

[22] Filed: Jul. 27, 1990

[51] Int. Cl.⁵ .................... C12N 5/12; C07K 15/28
[52] U.S. Cl. ........................ 435/240.27; 530/388.2; 530/388.4
[58] Field of Search ............... 530/387, 388.2, 388.4; 435/240.27; 935/104

[56] References Cited

OTHER PUBLICATIONS

*Biological Abstracts*, vol. 89, No. 5, Issued Mar. 1, 1990, V. V. Padhye et al., "Production and Characterization of Monoclonal Antibodies to Verotoxins 1 and 2 from *Escherichia coli* of Serotype 0157:H7", the abstract No. 48707, *J. Med. Microbiol.*, 1989, 30(3), 219-226.

*Gastroenterology*, vol. 94, No. 9, Issued Mar. 1988, S. Tzipori et al., "Studies in Gnotobiotic Piglets on Non-0157:H7 *Escherichia coli* Serotypes Isolated from Patients with Hemorrhagic Colitis," pp. 590-597, see the abstract.

*Journal of Clinical Microbiology*, vol. 26, No. 10, Issued Oct. 1988, L. P. Perera et al., "Isolation and Characterization of Monoclonal Antibodies to Shiga-Like Toxin II of Enterohemorrhagic *Escherichia coli* and Use of the Monoclonal Antibodies in a Colony Enzyme–Linked Immunosorbent Assay", pp. 2127-2131, see the Abstract.

Riley, Lee W. et al., 1983, "Hemorrhagic Colitis Associated With A Rare *Escherichia coli* Serotype," *The New England Journal of Medicine*, vol. 308, No. 12, pp. 681-685.

Levine, M. M. 1987, "*Escherichia coli* that Cause Diarrhea: Enterotoxigenic, Enteropathogenic, Enteroinvasive, Entrohemorrhagic, and Enteroadherent," *Journal of Infectious Diseases*, vol. 155, pp. 377-389.

Levine, M. M. et al., 1987, "A DNA Probe to Identify Enterohemorrhagic *Escherichia coli* of 0157:H7 and Other Serotypes that Cause Hemmorhagic Colitis and Hemolytic Uremic Syndrome," *Journal of Infectious Diseases*, vol. 156, pp. 175-182.

Ryan, Caroline A. et al., 1986, "*Escherichia coli* 0157:H7 Diarrhea in a Nursing Home: Clinical, Epidemiological, and Pathological Findings," *Journal of Infectious Diseases*, vol. 154, No. 4, pp. 631-638.

Doyle, Michael P. and Jean L. Schoeni, 1987, "Isolation of *Escherichia coli* 0157:H7 from Retail Fresh Meats and Poultry," *Applied and Environmental Microbiology*, vol. 53, No. 10, pp. 2394-2396.

Todd, E. C. D. et al., 1988, "Rapid Hydrophobic Membrane Filter–Enzyme Labeled Antibody Procedure for Identification and Enumeration of *Escherichia coli* 0157:H7 in Foods" *Applied and Environmental Microbiology*, vol. 54, pp. 2536-2540.

Samadpour, M. et al., 1990, "Evaluation of DNA probes for detection of Shiga–Like–Toxin Producing *Escherichia coli* in Food and Calf Fecal Samples," *Appl. and Envir. Microb.*, vol. 56, pp. 1212-1215.

Pollard, D. R. et al., 1990, "Rapid and Specific Detection of Verotoxin Genes in *Escherichia coli* by the Polymerase Chain Reaction," *J. Clin. Microb.*, vol. 28, pp. 540-545.

(List continued on next page.)

*Primary Examiner*—John J. Doll
*Assistant Examiner*—Susan L. Futrovsky
*Attorney, Agent, or Firm*—Andrus, Sceales, Starke & Sawall

[57] ABSTRACT

A monoclonal antibody specific for enterohemorrhagic *Escherichia coli* 0157:H7 and 026:H11 is produced by immunizing BALB/c mice with a strain of *E coli* 0157:H7. The antibody reacts strongly by an enzyme-linked immunosorbent assay with a 13,000 dalton molecular weight outer membrane protein of strains of enterohemorrhagic *Escherichia coli* 0157:H7 and 026:H11.

7 Claims, 1 Drawing Sheet

OTHER PUBLICATIONS

Padhye, V. V. et al., 1989, "Production and Characterization of Monoclonal Antibodies to Verotoxins 1 and 2 from *Escherichia coli* of Serotype 0157:H7," *J. Med. Microb.*, vol. 30, pp. 219–226.

Bopp, C. A. et al., 1987, "Unusual Verotoxin-Producing *Escherichia coli* Associated with Hemorrhagic Colitis," *J. Clin. Microbiol.*, vol. 25, pp. 1486–1489.

Karmali, M. A. et al., 1983, "Sporadic Cases of Hemolytic Uremic Syndrome Associated with Fecal Cytoxin and Cytoxin Producing *Escherichia coli* in Stools," *Lancet*, vol. i, pp. 619–620.

Perry, M. B. et al., 1988, "Identification of *Escherichia coli* Serotype 0157 Strains by Using a Monoclonal Antibody," *J. Clin. Microbiol.*, vol. 26, pp. 1973–1978.

Smith et al., 1985, "Measurement of Protein Using Bicinchoninic Acid," *Analytical Biochemistry*, vol. 150, pp. 76–85 (determination of protein concentration).

Hancock, R. E. W. and H. Naikaido, 1987, "Outer Membranes of Gram-Negative Bacteria," *Journal of Bacteriology*, vol. 136, pp. 381–390 (isolating of outer membrane proteins).

Padhye, N. P. and M. P. Doyle, 1990, "Production and Characterization of Monoclonal Antibody to *Escherichia coli*" 0157:H7, *Amer. Soc. for Microb.* (Annual Mtg.) (Abstract) p. 14.

MONOCLONAL ANTIBODY TO ENTEROHEMORRHAGIC ESCHERICHIA COLI 0157:H7 AND 026:H11

FIELD OF THE INVENTION

The present invention relates generally to hybridoma cell lines developed to produce monoclonal antibodies and, more specifically, to a cell line producing monoclonal antibodies to enterohemorrhagic *Escherichia coli* 0157:H7 (*E. coli* 0157:H7) and *Escherichia coli* 026:H11 (*E. coli* 026:H11).

DESCRIPTION OF THE PRIOR ART

*E. coli* 0157:H7 was first recognized as an important human pathogen in the United States in 1982, when the organism was diagnosed as the cause of two geographically separate outbreaks of hemorrhagic colitis, both associated with eating undercooked beef from a particular fast-food chain, (Riley, Lee W. et al, 1983, "Hemorrhagic Colitis Associated With A Rare *Escherichia Coli* Serotype," *The New England Journal of Medicine* Vol. 308, No. 12, pgs. 681-685). These outbreaks of unusual gastrointestinal illness were characterized by the sudden onset of severe abdominal cramps and grossly bloody diarrhea with no fever or low grade fever. Such illnesses have been associated with *E. coli* 0157:H7 and also *E. coli* 026:H11 (Levine, M. M. 1987, "*Escherichia coli* that Cause Diarrhea: Enterotoxigenic, Enteropathogenic, Enteroinvasive, Enterohemorrhagic, and Enteroadherent," *Journal of Infectious Diseases*, Vol. 155, pgs. 377-389; Levine, M. M., et al., 1987, "A DNA Probe to Identify Enterohemorrhagic Escherichia coli of 0157:H7 and Other Serotypes that Cause Hemmorhagic Colitis and Hemolytic Uremic Syndrome," *Journal of Infectious Diseases*. Vol. 156, pgs. 175-182). These bacteria are termed enterohemorrhagic *E. coli*.

The *E. coli* organism produces toxins, known as verotoxins, that cause significant intestinal bleeding in several mammals, including humans. The spectrum of illnesses associated with *E. coli* 0157:H7 infections ranges from asymptomatic infections to non-bloody diarrhea, hemorrhagic colitis, hemolytic uremic syndrome and death (Ryan, Caroline A. et al, 1986, "*Escherichia coli* 0157:H7 Diarrhea in a Nursing Home: Clinical, Epidemiological, and Pathological Findings," *Journal of Infectious Diseases*, Vol. 154, No. 4, pgs. 631-638). Hemolytic uremic syndrome is defined as the sudden onset of hemolytic anemia, thrombocytopenia and acute renal failure after the appearance of symptoms in the upper respiratory tract, stomach or intestines. Hemolytic uremic syndrome is generally the end result of a number of different and inciting events and pathogenic mechanisms.

The organism has been isolated from meat and poultry and unpasteurized milk. A variety of reports suggest that foods, particularly foods of animal origin, may be an important source of *E. coli* 0157:H7 infections (Doyle, Michael P. and Jean L. Schoeni, 1987, "Isolation of *Escherichia Coli* 0157:H7 from Retail Fresh Meats and Poultry," *Applied and Environmental Microbiology*, Vol. 53, No. 10, pgs. 2394-2396).

Because most of the outbreaks of hemorrhagic colitis have been food related, there is a need for a rapid, sensitive and specific assay for detecting *E. coli* 0157:H7 and *E. coli* 026:H11. Presently, the available methods for detecting the organism in foods are time consuming or are not highly specific. For example, the Food Research Institute, Madison, Wis., is currently being used by many agencies for the detection of the *E. coli* 0157:H7 organism. The process utilized by the Food Research Institute, however, involves a complicated, multi-day procedure described in Doyle and Schoeni (supra). Doyle and Schoeni have tested a variety of meats and found the organism in about 1% or 2% of the meats tested. The organism can also be isolated from feces, raw milk, etc. Eggs from experimentally infected chickens are also contaminated on the surface.

In order to assay the organism, the first step is to enrich the organism in the food sample. Because the food sample may have minor amounts of the organism, the sample is placed in an enrichment medium to put it in a condition which should repress other forms of bacteria and increase the numbers of the desired organism. The enrichment medium has selective agents which are selective for gram-negative bacteria, including *E. coli* 0157:H7. The medium is then incubated overnight at 37° C.

The incubated sample is then run through a hydrophobic grid membrane filter paper (HGMF). The filter paper is subdivided into about 1,400–1,600 little squares. Wax is used to mark the filter off. The wax keeps the colonies isolated. The filter is then removed and placed on a piece of nitrocellulose paper. The nitrocellulose paper will be placed over some of the medium with agar that contains the same selective agents as in the enrichment medium. This plate is then incubated at 37° C. overnight. This allows the colonies to develop on the filter paper. As they grow, they elaborate verotoxins. The toxins are trapped in the nitrocellulose paper. The filter paper is then removed and saved. The nitrocellulose paper is then removed and developed by an immunoblot procedure which employs antibodies produced in rabbits to the toxins. After the blots are developed, spots are observed on the paper where toxin is present. The spots on the HGMF are matched with the bacterial colonies on the HGMF, and the matching colonies are then confirmed as the target *E. coli* 0157:H7 by biochemical or other tests.

In summary, the organism is grown in the food sample in a selective enrichment medium. The organism is then isolated in a series of procedures. The separated isolates grow to produce toxins which diffuse into and are entrapped in an underlying filter paper. The toxins are then detected using antibody to the toxins as a reagent. Bacterial colonies on the overlying filter paper with grids are aligned with the filter paper showing sport with toxin. Colonies that produced toxin are identified by standard taxonomic procedures.

Although the procedure can effectively isolate *E. coli* 0157:H7 from food samples inoculated with low levels of the organism, the method is not amenable to routine testing because of complexity and extensive need for personnel time.

Other tests, such as one developed by Health and Welfare Canada, are being developed. The Canadian test uses a monoclonal antibody to *E. coli* 0157, but it is not a specific test because it cross-reacts with other enterics, such as Salmonella Group N and unimportant *E. coli* 0157 strains that are not H7. (Todd, E. C. D. et al, 1988, "Rapid Hydrophobic Membrane Filter-Enzyme Labeled Antibody Procedure for Identification and Enumeration of *Escherichia coli* 0157:H7 in Foods" *Applied and Environmental Microbiology*, Vol. 54, pgs. 2536-2540.)

Gene-probe based assays have been developed which are based on binding DNA that encodes for verotoxins (Samadpour, M. et al., 1990, "Evaluation of DNA probes for detection of Shiga-Like-Toxin Producing *Escherichia coli* in Food and Calf Fecal Samples," *Appl. and Envir. Microb.*, Vol. 56, Pgs. 1212-1215; Pollard, D. R. et al., 1990, "Rapid and Specific Detection of Verotoxin Genes in *Escherichia coli* by the Polymerase Chain Reaction," *J. Clin. Microb.*, Vol 28, Pgs. 540-545.). Hence, all verotoxin-producing *E. coli* are detected by this procedure rather than solely enterohemorrhagic *E. coli* 0157:H7 and *E. coli* 026:H11.

SUMMARY OF THE INVENTION

It is an object of the present invention to produce a monoclonal antibody that is highly specific for enterohemorrhagic *E. coli* 0157:H7 and *E. coli* 026:H11.

It is further an object of the present invention to develop a test for using a monoclonal antibody to assay *E. coli* 0157:H7 and *E. coli* 026:H11 in which the procedure is shortened to a usable period of time, e.g., under one day.

It is further an object of the present invention to develop an immunoassay for the rapid detection of *E. coli* 0157:H7 and *E. coli* 026:H11 in food and fecal specimens.

It is another object of the present invention to develop a procedure to isolate *E. coli* 0157:H7 and *E. coli* 026:H11 from foods or other samples and to determine the prevalence of the organisms in the samples.

It is another object of this present invention to use the approximately 13,000 dalton molecular weight outer membrane protein of enterohemorrhagic *E. coli* 0157:H7 and *E. coli* 026:H11 as a marker to identify strains of enterohemorrhagic *E. coli*. Assays, including ELISA, based on monoclonal antibody specific to this marker, will be used to detect and differentiate enterohemorrhagic *E. coli* isolated from foods, environmental and clinical specimens.

It is further an object of the present invention to provide for the synthesis of a bioreagent for antibody assays, which will be useful in a test kit for, for example, assaying the presence of enterohemorrhagic *E. coli* 0157:H7 and *E. coli* 026:H11.

The present invention is summarized in that a monoclonal antibody specific to enterohemorrhagic *E. coli* 0157:H7 and *E. coli* 026:H11 is produced by a hybridoma formed by the fusion of cells from a mouse myeloma line and spleen cells from a mouse previously immunized with a "rough" strain of *E. coli* 0157:H7. This rough strain was modified so that it lacks smooth lipopolysaccharides, which includes expression of 0157 antigen, on its cell surface. The monoclonal antibody is characterized in that it reacts with a protein having a molecular weight of approximately 13,000 daltons, and it is a part of the outer membrane proteins of enterohemorrhagic *E. coli* 0157:H7 and *E. coli* 026:H11. This protein has apparent specificity for enterohemorrhagic *E. coli* 0157:H7 and *E. coli* 026:H11. The monoclonal antibody is further characterized in that it is a member of the subclass immunoglobulin $G_{2a}$ and it has a kappa light chain.

The present invention is further directed to a method of assaying for the presence of *E. coli* 0157:H7 in a test sample, comprising the steps of binding polyclonal antibody to *E. coli* 0157 to adsorptor substrate units to produce antibody to *E. coli* 0157-charged substrate units, exposing a known quantity of the test material to the antibody *E. coli* 0157-charged substrate unit so as to cause the antibody to bind to any *E. coli* 0157:H7 organism present in the test material to produce a reacted unknown sample, exposing a selected quantity of a standard preparation of *E. coli* 0157:H7 organism having a known amount of *E. coli* 0157:H7 to the antibody to *E. coli* 0157-charged substrate unit to create a reacted control sample, exposing the reacted unknown and control samples to a monoclonal antibody, designated 4E8C12, to *E. coli* 0157:H7 to react with the bound *E. coli* 0157:H7, removing monoclonal antibody not reacted with the bound *E. coli* 0157:H7 on the antibody to *E. coli* 0157-charged substrate units and comparatively and quantitatively assaying for the presence of reacted monoclonal antibody on the first and second antibody to *E. coli* 0157-charged substrate units.

The present invention is further directed to a process for producing monoclonal antibodies against enterohemorrhagic *E. coli* 0157:H7 and *E. coli* 026:H11 comprising propagating a hybridoma formed by fusing a cell capable of producing antibodies against enterohemorrhagic *E. coli* 0157:H7 and *E. coli* 026:H11 with a myeloma cell and harvesting the antibodies produced by the hybridoma.

The present invention is also directed to a diagnostic kit for assaying the presence of enterohemorrhagic *E. coli* 0157:H7 and/or *E. coli* 026:H11 comprising the monoclonal antibody specific to enterohemorrhagic *E. coli* 0157:H7 and *E. coli* 026:H11 and directions for its use.

The present invention is also directed to a bioreagent for antibody assays comprising a substantially pure protein having a molecular weight of about 13,000 daltons. The protein is found in the outer membrane of *E. coli* 0157:H7 or *E. coli* 026:H11, and is capable of reacting specifically with monoclonal antibodies to *E. coli* 0157:H7 and *E. coli* 026:H11.

The present invention is also directed to a substantially pure protein found in the outer membrane of *E. coli* 0157:H7 or *E. coli* 026:H11 having a molecular weight of about 13,000 daltons and being capable of reacting specifically with monoclonal antibodies to *E. coli* 0157:H7 and *E. coli* 026:H11.

Because of its high specificity, the monoclonal antibody may be a useful reagent for the rapid detection of enterohemorrhagic *E. coli* 0157:H7 and/or *E. coli* 026:H11 in foods and in clinical specimens. Further, the testing procedure should be reduced to one day or less. The testing procedure would include, first, growing the organism on a selected growth medium and, then, testing for its presence by, for example, enzyme-linked immuno-sorbent assays (hereinafter ELISAs) and other immunoassays.

Other objects and advantages of the invention will be apparent from the following detailed description and figure setting forth the preferred embodiment of the invention.

DETAILED DESCRIPTION OF THE PREFERRED EMBODIMENT

Figure 1:
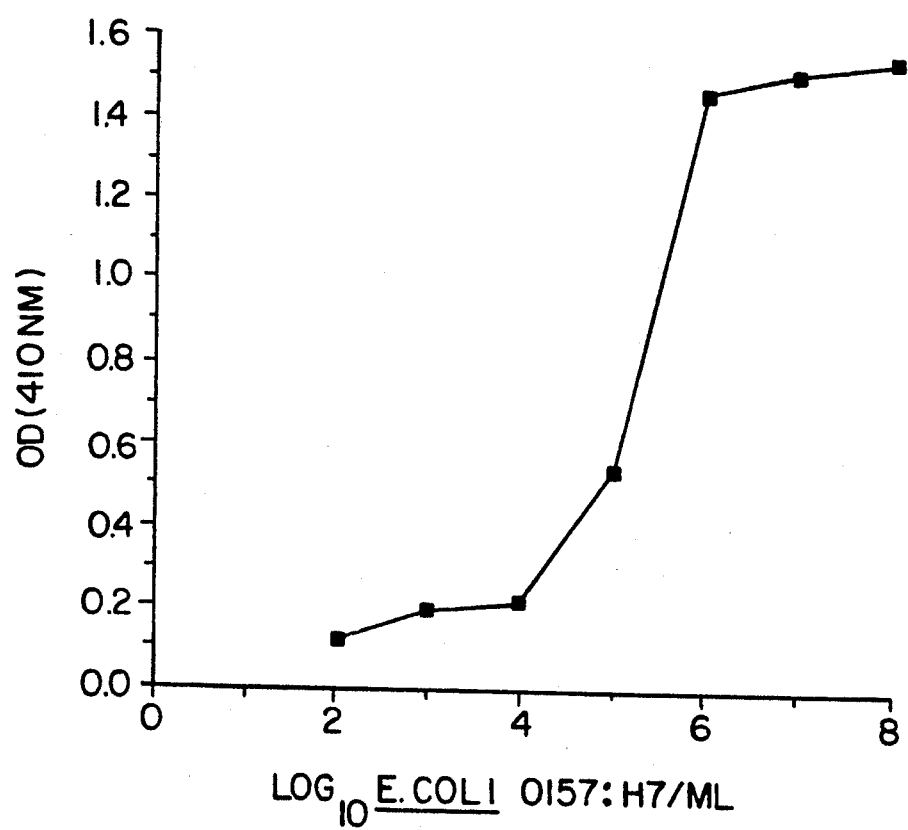
FIG. 1 is a graph illustrating the sensitivity of the monoclonal antibody 4E8C12 in a direct ELISA for detecting *E. coli* 0157:H7, strain 932, as described in Example II.

Enterohemorrhagic *E. coli* 0157:H7 and *E. coli* 026:H11 have been identified as important human pathogens. They produce one or more toxins (verotoxins) that cause significant intestinal bleeding in several mammals, including humans. The organism is sometimes fatal. It is found in raw milk, raw supermarket meats, etc. and presumably introduced by fecal contamination. Some of the characteristics of *E. coli* 0157:H7, as described in Ryan et al (supra, 1988), are as follows. *E. coli* 0157:H7 does not produce heat stable or heat labile enterotoxins. It is not invasive and does not adhere to HeLa cells. It does produce high levels of a Vero cytotoxin that appears to be similar to Shiga toxin. *E. coli* has been shown to produce one or more different Vero cell cytotoxins, as described in Padhye, V. V. et al., 1989, "Production and Characterization of Monoclonal Antibodies to Verotoxins 1 and 2 from *Escherichia coli* of Serotype 0157:H7," *J. Med. Microb.*, Vol. 30, pgs. 219-226.

*E. coli* 026:H11 is similar to *E. coli* 0157:H7 in that both are enterohemorrhagic *E. coli* that produce verotoxin and cause hemolytic uremic syndrome and hemorrhagic colitis (Bopp, C. A., et al., 1987, "Unusual Verotoxin-Producing *Escherichia coli* Associated with Hemorrhagic Colitis," *J. Clin. Microbiol.*, Vol. 25, pgs. 1486-1489; Karmali, M. A. et al., 1983, "Sporadic Cases of Hemolytic Uremic Syndrome Associated with Fecal Cytoxin and Cytoxin Producing *Escherichia coli* in Stools," *Lancet*, Vol. i, pgs. 619-620; Levine, M. M., supra., 1987).

In general overview, a monoclonal antibody, designated 4E8C12, specific for *E. coli* 0157:H7 and *E. coli* 026:H11 was produced by immunizing BALB/c mice with a "rough" strain of *E. coli* 0157:H7 deficient of the 0157 antigen. Spleen cells from the mice so immunized were fused with a mouse myeloma cell, with the fusion being effected with treatment in polyethylene glycol in accord with known methods. The resulting hybridomas were cultured and then selected for antibody activity. The cells producing antibodies specific to *E. coli* 0157:H7 and *E. coli* 026:H11 were detected by means of an ELISA, in the manner well known to the art. The antibody was purified from ascites fluid in conventional ways. The cloned cell line so created and selected was perpetuated by conventional cell culturing techniques.

The hybridoma produced in this manner was deposited at the American Type Culture Collection 12301 Parklawn Drive, Rockville, Md. 20852, USA on May 10, 1990, and has been assigned the designation HB 10452. This particular hybridoma and the antibodies produced thereby are the hybridoma and monoclonal antibodies referred to below, unless otherwise stated. A detailed description of the making of the hybridoma is included below. Future reference to the hybridoma is as follows: ATCC HB 10452.

In contrast with previously reported references, which disclose monoclonal antibodies that react with *E. coli* 0157:H7 but also bind to the somatic 0157 antigen and hence react with all *E. coli* belonging to the serogroup 0157 (Perry, M. B. et al., 1988, "Identification of *Escherichia coli* Serotype 0157 Strains by Using a Monoclonal Antibody," *J. Clin. Microbiol.*, Vol 27, pgs. 1973-1978), the monoclonal antibody of the present invention does not react with the 0157 antigen and is, with the exception of one other serotype of *E. coli*, very specific for *E. coli* 0157:H7. The other serotype is *E. coli* 026:H11. As used herein, the phrase "specific for *E. coli* 0157:H11 and *E. coli* 026:H7" is intended to mean that the monoclonal antibody of the present invention does not react with the strains of *E. coli* listed on Table 1 in Example 1, infra other than the listed strains of *E. coli* 0157:H7 and *E. coli* 026:H11.

The antibodies were tested for specificity by ELISAs and by immunoblotting of a variety of enterics. By these means, it was determined that the monoclonal antibody forms a strong reaction by direct ELISA with each of 36 strains of *E. coli* 0157:H7 and 5 strains of *E. coli* 026:H11. However, there was no cross-reactivity with strains of other enterics such as, for example, Salmonella, *Yersinia entrocolitica*, Shigella, Proteus, Klebsiella, *Campylobacter jejuni*, Serratia, *Aeromonas hydrophila*, Citrobacter, Enterobacter, Hafnia, *Escherichia hermanii*, and all other strains of *E. coli* other than the serotypes 0157:H7 and 026:H11 (including strains of serotype 0157 but not H7).

Studies on the monoclonal antibody to *E. coli* 0157:H7 and 026:H11 show that the monoclonal antibody has the following characteristics: (1) it is a member of the subclass $IgG_{2a}$; (2) it has a kappa light chain; and (3) it reacts specifically with an outer membrane protein of enterohemorrhagic *E. coli* 0157:H7 and *E. coli* 026:H11 having a molecular weight of 13,000 daltons, as determined by SDS-polyacrylamide gel electrophoresis of outer membrane proteins of *E. coli* of different serotypes followed by Western blot analysis.

ELISAs are a conventional method for assaying for the presence of an antigen in a sample of test material. The sandwich ELISA of the invention is adapted to assay for the presence of enterohemorrhagic *E. coli* 0157:H7 in a sample of test material and includes the following steps. First, a known antibody to *E. coli* 0157 is bound to a suitable adsorbtor substrate. Preferably, a plastic culture plate is used, such as a 96-well polystyrene culture plate (Costar, Cambridge, Mass.—Model No. 3596). A solution of antibody to *E. coli* 0157 is placed in each of the wells and allowed to remain under conditions such that the antibody to *E. coli* 0157 is adsorbed to the surface of the wells. Unadsorbed antibody solution is then washed away, leaving the antibody to *E. coli* 0157 bound to the adsorptive walls of the wells, which shall be referred to as "adsorbtor substrate units." With antibody to *E. coli* 0157 adsorbed to them, they shall be referred to as "antibody to *E. coli* 0157-charged substrate units." The antibody to *E. coli* 0157-charged substrate units is then treated with an appropriate blocking reagent, such as nonfat dried milk, to block non-specific binding sites. After appropriate incubation, this reagent is removed.

Next, a known quantity of the test material is exposed to the antibody to *E. coli* 0157-charged substrate units for an appropriate period of time, and then is removed by washing. Any *E. coli* 0157:H7 in the test material will bind to the antibody to *E. coli*-charged substrate units.

Similarly, a standard preparation of *E. coli* 0157:H7 is exposed to another set of antibody to *E. coli* 0157-charged substrate units to serve as a control.

The monoclonal antibody referred to above is added to the antibody to *E. coli* 0157-charged substrate units to bind with any bound *E. coli* 0157:H7. After appropriate incubation, unbound the monoclonal antibody is removed by washing.

The antibody to *E. coli* 0157-charged substrate units reacted with test samples or *E. coli* 0157:H7 are then assayed for the presence of monoclonal antibody.

Preferably this is done by exposing antibody to *E. coli* 0157-charged substrate units reacted with the test samples or *E. coli* 0157:H7 and the monoclonal antibody thereon to a marker-coupled anti-mouse antibody to allow the marker-coupled antibody to bind to any monoclonal antibody present. The unbound marker-coupled antibody is then removed, and the amount of marker remaining on the antibody to E. coli 0157-charged substrate units is measured. The marker may be an enzyme measured by its effect on a selected reagent, a fluorescent material, a radioactive material, or any other of the markers familiar to one skilled in the art. It will be apparent that the monoclonal antibody itself may be combined directly with a marker, whereupon the step of reacting a marker-coupled anti-mouse antibody may be omitted.

The monoclonal antibody may also be used in other conventional ELISAs. For example, a sample of test material may be bound to an adsorbtor substrate and then exposed to the monoclonal antibody disclosed above. The antibody binds to any E. coli 0157:H7 or E. coli 026:H11 present in the test material. Unbound portions of the monoclonal antibody are then removed. Next, an assay comparable to those discussed above is conducted for the presence of bound monoclonal antibody.

The monoclonal antibody of the present invention may also be used in any of the generally known methods of using such antibodies in immunohistological techniques for examining a substantially cohesive, nonfluid test material, such as a cell or tissue sample. Preferably, the sample is a food product or a fecal sample. The test material is incubated with the monoclonal antibody to bind the antibody to E. coli 0157:H7 or E. coli 026:H11 present in the test material. The test material is then washed to remove the unbound portion of the monoclonal antibody. The antibody may then be reacted in such a way as to make its presence visually apparent. Typically, the test material bearing monoclonal antibody bound to E. coli 0157:H7 or E. coli 026:H11 contained therein is incubated with a marker-labeled anti-mouse antibody comparable to those discussed above. The marker-labeled antibody binds to the monoclonal antibody. A marker is selected such that it may be made visually apparent. Fluorescent and enzyme markers typically are used. The test material is then microscopically observed under conditions adapted to render the marker visually perceivable. The monoclonal antibody to E. coli 0157:H7 and E. coli 026:H11 is specifically useful as a reagent for the rapid detection of E. coli 0157:H7 and/or E. coli 026:H11 in food and clinical specimens.

The present invention also includes kits, e.g., diagnostic assay kits, for utilizing the monoclonal antibody to E. coli 0157:H7 and E. coli 026:H11 and carrying out the method disclosed above. In one embodiment, the diagnostic kit would conventionally include the monoclonal antibody to the E. coli 0157:H7 and E. coli 026:H11 in one or more containers, a conjugate of a specific binding partner for the monoclonal antibody, a label capable of producing a detectable signal, and directions for its use. The kit may be conjugated to a label, as is well known to the art. Various labels include enzymes, radioisotopes, particulate labels, chromogens, fluorescers, chemiluminescers, coenzymes, free radicals, and bacteriophages. Additionally the monoclonal antibody may be bound to a support.

A specific diagnostic kit could be in a dipstick format. This could involve adsorbing polyclonal E. coli 0157 immunoglobulin to a hydrophobic polyvinylidene difluoride (PVDF)-based membrane. The PVDF membrane is then treated with 5% bovine serum albumin to block nonspecific binding sites. The PVDF membrane is dipped for 30 minute in an enrichment culture of food that may contain E. coli 0157:H7. After washing, the PVDF membrane is treated with monoclonal antibody 4E8C12. This antibody will bind to any E. coli 0157:H7 cells bound to the PVDF membrane. The bound monoclonal antibody 4E8C12 is detected with alkaline phosphatase-conjugated goat anti-mouse immunoglobulin that reacts with Nitro blue tetrazolium/5-bromo-4-chloro-3-indolylphosphate substrate to produce purple spots as a positive reaction.

The 13,000 dalton molecular weight protein found in the outer membrane of E. coli 0157:H7 and E. coli 026:H11 can also be isolated as a bioreagent and used to prepare monoclonal antibodies for detection of E. coli 0157:H7 and E. coli 026:H11 in a sample. The monoclonal antibodies can be provided in test kits which are used to diagnose cases of suspected E. coli 0157:H7 and E. coli 026:H11 contamination.

The examples below provide specific examples of the invention disclosed herein.

EXAMPLE I

Preparation of the Cloned Cell Line

Bacterial cultures used to identify specificity of monoclonal antibody: The following strains of bacteria were studied in these examples: E. coli 0157:H7 strain 932; E. coli HA1 (a rough strain derived from E. coli 0157:H7 932), thirty-four other strains of E. coli 0157:H7, as listed in the following Table 1, five strains of E. coli 026:H11, and thirty-seven strains of E. coli other than 0157:H7 or 026:H11, as listed in the following Table 1:

TABLE 1

| Bacterial Strains Studied | |
| --- | --- |
| | Strain No. |
| E. coli Serotype 0157:H7 | 932 |
| | 1083-83 |
| | CL-8 |
| | 1215-83 |
| | CL-40 |
| | 936-86 |
| | 204-P |
| | W2-2 |
| | EC-13 |
| | 100B |
| | RPS 386-1 |
| | EC-12 |
| | SL-19808 |
| | 1091-83 |
| | A8187 M3 |
| | EC-14 |
| | 1093-83 |
| | SL-20069 |
| | NX 0157:H7 |
| | 1095-83 |
| | 202-P |
| | RPS-779 |
| | 749-83 |
| | HA1 |
| | 2790 |
| | 28890 |
| | 85-1 |
| | 85-7 |
| | 86-1 |
| | 86-7 |
| | 87-3 |
| | 87-18 |
| | 30898-1 MUG |
| | 933 |
| | 505-B |
| | 301-C |
| E. coli other than serotype 0157:H7 | 929-78 |
| | C-600 933W |

TABLE 1-continued

Bacterial Strains Studied

| | Strain No. |
|---|---|
| | 933-J |
| | EC PB40 |
| | EC GV50B |
| | EC PB-200 |
| | EC PB-175 |
| | K88 |
| | K99 |
| | RSF 1030 |
| | E. coli R1 |
| | RP4 |
| | E. coli K-12 |
| | 88-1947 (0157:H16) |
| | A2 (0157:H19) |
| | 84-1097 (0157:H25) |
| | 624-83 (0157:H45) |
| | OPHD (0157:H-) |
| | 88-573 (02:H7) |
| | 88-766 (018:H7) |
| | CL-15 (0113:H21) |
| | CL-37 (0111:H8) |
| | 497-18 (028ac:NM) |
| | 0128:B12 |
| | 3288-85 (0172:NM) |
| | 3056-85 (050:H7) |
| | 3030-86 (011:NM) |
| | 3377-85 (04:NM) |
| | 3153-86 (0125:NM) |
| | 75-83 (0145:NM) |
| | A96119-C2 (045:H2) |
| | 3143-85 (05:NM) |
| | 3007-85 (0111:NM) |
| | 88-573 (026:H11) |
| | 84-381 (026:H11) |
| | 105B |
| | A-2028 |
| | CL-5 (026:H11) |
| | 89-386 (026:H11) |
| | 3047-86 (026:H11) |
| Shigella dysenteriae | 4386 |
| | 6611 |
| Escherichia hermanii | 89-201 |
| Proteus mirabilis | SLH 16606 |
| | MC-3 |
| Proteus vulgaricus | 8068 |
| Serratia marcescens | 23521 |
| Salmonella infantis | 1-2 |
| | 5 |
| | 6S |
| Salmonella urbana | 9261 |
| Salmonella enteritidis | 11013 |
| Salmonella typhimurium | S-7 |
| | S-9 |
| | S-12 |
| | S-15 |
| | E 1297 |
| | S-14 |
| | S-18 |
| | S-19 |
| | E-40 |
| | 9840 |
| Campylobacter jejuni | FRI 209 |
| | FRI 205 |
| | FRI 145 |
| | 74C |
| | C122 |
| Klebsiella pneumoniae | 272-6 |
| | F182-5(1) |
| | F182-5(2) |
| | F182-6(1) |
| | F184-5(4) |
| | F184-5(5) |
| | F184-6(1) |
| | F188-5(4) |
| | F189-5(2) |
| | F189-5(3) |
| | F189-6(1) |
| | F190-6(3) |
| | F190-7(5) |
| Klebsiella oxytoca | 11696 |

TABLE 1-continued

Bacterial Strains Studied

| | Strain No. |
|---|---|
| Citrobacter fruendii | Y6₁10RS |
| | A2₄4R1 |
| | 8027 |
| | JF1 |
| Citrobacter amalanticus | 28422 |
| Cibrobacter freundii | MAT-8 |
| | 6 |
| Citrobacter diversus | MA₁S-9 |
| | MA₄S-9 |
| | 275-6 |
| | LMH 5 |
| | 274-8 |
| Yersinia enterocolitica | IP-183 |
| | IP-162 |
| | 2635-NT |
| | 34 |
| | 30118 |
| | 705 |
| | 675 |
| | PT-120 |
| | Y-7P |
| | PT-63 |
| | 736 |
| | WA |
| Enterobacter cloacae | 274-6 |
| | 272-6 |
| Hafnia alvei | CB-7 |
| Aeromonas hydrophila | 7 |
| | 12 |
| | 17 |
| | 23 |

All bacteria were grown in Trypticase ® Soy Broth (TSB) (BBL Microbiology Systems, Cockeysville, Md.) at 37° C. for 16–18 hours with agitation (100 rpm).

Toxins: Verotoxins-1 (VT-1) and Verotoxin-2 (VT-2) from E. coli 0157:H7 strain 932 were purified according to the procedures described by Padhye et al. (supra).

Preparation of antigen for inoculation: E. coli HA1 cells were grown in TSB at 37° C. for 16 hours with agitation (100 rpm). The cells were harvested by centrifugation (3500 rpm for 10 minutes) and were washed 3 times with 0.01 M phosphate buffered saline (pH 7.2). E. coli HA1 cells were treated with 2% Formalin and held at 37° C, for 1 week.

Ten BALB/c mice (males, 6–8 weeks old) were immunized by intraperitoneal injection of $2 \times 10^8$ cells of Formalin-treated E. coli HA1. Thereafter, every 4 weeks the mice received intraperitoneally the same number of Formalin-treated cells of E. coli HA1 until sera obtained by periodic bleeding of mice had titers greater than 1:400. This generally required 3 inoculations. Four days before cell fusion, the mice were given a final intravenous booster injection of $1 \times 10^8$ Formalin-treated cells of E. coli HA1. Four to five months after the initial injection, mice were sacrificed and their spleen cells were fused with myeloma cells.

Fusion and cloning: The fusion and cloning process was performed according to the procedure of Galfre, G., 1981, "Preparation of Monoclonal Antibodies: Strategies and Procedures," Methods in Enzymology, Vol. 73, pgs. 1–46.) with minor modifications. Briefly, spleen cells from the immunized mice were fused with Sp2/0-Ag-14 myeloma cells using 40% polyethylene glycol (Molecular weight, 1300-1600) (J. T. Baker Chemical Co., Phillipsburg, N.J.) and were grown in selective media containing hypoxanthine, aminopterine, and thymidine (HAT) with 0.3% mouse red blood cells. Supernatant fluids from wells with hybridoma growth were screened for the production of antibodies against *E. coli* 0157:H7 by direct ELISA as described below. Hybridomas of interest were sub-cloned twice by the method of Kohler & Milstein (1975) *Nature*, Vol. 256, pgs. 495–497, by limiting dilution at 0.5 and 0.1 cell/well in a media containing 20% fetal bovine serum (Gibco, Grand Island, N.Y.) and reassayed for antibody production.

Direct ELISA: Antibody production was determined by ELISA performed in a 96-well styrene EIA-RIA plate (Gibco, Grand Island, N.Y.). Each well was coated with 100 microliters (ul) of bacterial cells (*E. coli* 0157:H7 strain 932, *E coli* 0157:H16, *E. coli* 02:K1:H7, or *E. coli* K-12 (negative control) or $10^7$ cells, optical density of 0.5 at 640 nm) in 50 mM carbonate buffer, pH 9.6, and rotated overnight on an orbital shaker at room temperature. After washing the cells 4 times with 50 mM tris-HCl, pH 7.5, plus 150 mM NaCl (TBS), the remaining binding sites were blocked with 5% BSA in TBS. After 1 hour of incubation at 37° C., the blocking buffer was removed and 100 ul of monoclonal antibody (hybridoma supernatant fluid) was added to the wells. The plates were incubated at 37° C. for 1 hour and then the wells were washed 4 times with TBS plus 0.05% Tween-20 (TBS-T). Horseradish peroxidase-conjugated goat anti-mouse IgG (100 ul/well; 1:1400 in TBS) (Kirkegaard & Perry Laboratory, Inc. Gaithersburg, Md.) was added and incubated at 37° C. for 1 hour. After washing the wells 4 times with TBS-T, 100 ul of ABTS-peroxidase substrate (Kirkegaard & Perry Laboratories, Gaithersburg, Md.) was added per well. The enzymatic reaction was stopped with 50 ul of 1% sodium dodecyl sulfate (SDS) in TBS per well after 15 minutes incubation at room temperature. The optical density of reactants in each well was measured by a Dynatech (MR300) microplate reader at 410 nm. Reproducibility of the assay was determined by duplicate testing.

Ascitic fluid: Ten BALB/c mice were primed by intraperitoneal injection of 0.5 ml of 2, 6, 10, 14-tetramethyl pentadecane (Pristane) (Sigma Chemical Co., St. Louis, Mo.). Ten days later mice were injected with $2 \times 10^6$ hybridoma cells. Mouse ascitic fluid was collected from 10 through 20 days after injection. Cell debris and fibrin clots were removed by centrifugation (8000 xg at 10 minutes) and antibody containing fluids were stored at $-20°$ C.

Purification of monoclonal antibodies: The monoclonal antibody from the ascitic fluid was purified according to a modification of the manufacturer's instructions using a protein A column (Immunopure plus IgG purification kit, Pierce, Rockford, Ill.). Briefly, ascitic fluid was centrifuged at 10,000 xg for 20 minutes and IgG-binding buffer was added (3:1) to the supernatant fluid. This solution (4 ml) was applied to the column and the monoclonal antibody was eluted with IgG-elution buffer. One-ml fractions were collected and protein levels were monitored by measuring (optical density at 280 nm). Fractions with proteins were combined and were dialyzed against 20 mM phosphate buffer, pH 7.0, overnight at 4° C. Finally, the protein concentration was determined according to the procedure described by Smith et al., 1985, "Measurement of Protein Using Bicinchoninic Acid," *Analytical Biochemistry*, Vol. 150, pgs. 76–85, using Pierce BCA protein reagent (Pierce Chemical Co., Rockford, Ill.) and bovine serum albumin as a standard. The activity of purified antibody was determined by direct ELISA and purity was determined by SDS-PAGE.

Immunoglobulin isotyping: Immunoglobulin isotyping was done by ELISA using class specific antisera. Wells of EIA plates were coated with *E. coli* 0157:H7 strain 932 ($10^7$ cells/ml) in 50 mM carbonate buffer (pH 9.6). After 4 washes with TBS, nonspecific binding sites were blocked with 5% bovine serum albumin in TBS (W/V). After 1 hour incubation at 37° C., 0.1 ml of the supernatant containing monoclonal antibody 4E8C12 was added to each well and incubation was continued for an additional hour at 37° C. After washing the wells 4 times with TBS-T, rabbit antisera specific individually for mouse IgG, $IgG_{2a}$, $IgG_{2b}$, $IgG_3$, IgM, IgA, kappa or lambda light chains (Mouse-types Isotyping kit, Bio-Rad Laboratories, Richmond, Calif.) were added and held at 37° C. for one hour. The wells were washed 4 times with TBS-T and alkaline phosphatase-labeled goat anti-rabbit IgG (0.1 ml; diluted 1:800 in TBS) was added to each well followed by incubation at 37° C. for 1 hour. After washing the wells 4 times with TBS-T, phosphatase substrate (p-nitrophenylphosphate) (1.0 mg/ml) in 1.0 M 2 amino-2 methyl-1-propanol, pH 9.9, was added and an optical density at 410 nm was determined after 1 hour incubation at 37° C.

Preparation of outer-membrane proteins: Outer membrane proteins (OMP) were isolated according to the method described by Hancock and Naikaido (Hancock, R. E. W. and H. Naikaido, 1987, "Outer Membranes of Gram-Negative Bacteria," *Journal of Bacteriology*, Vol. 36, pgs. 381–390.), with minor modifications. *E. coli* 0157:H7 strain 932, *E. coli* HA1, *E. coli* 0157:H16, *E. coli* 0157:H45, and *E. coli* CL-5 6026:K-60:H11 were grown individually in 2 liters of TSB at 37° C. for 18 hours with agitation (150 rpm). Cells were harvested by centrifugation (10,000 xg for 10 minutes at 4° C.) and subsequent operations were performed at 4° C. Cells were washed with 0.01 M phosphate buffer, pH 7.2, containing 170 mM NaCl (PBS), sedimented by centrifugation, and the pellets were resuspended in the same buffer to a calculated optical density of 40 at 640 nm. Cells were broken in a French Press (1400 lb/in$^2$) (American Instrument Company, Silver Spring, Md.) and cell debris was removed by centrifugation (5000 xg for five minutes). OMP were sedimented from the supernatant fluid by centrifugation at 200,000 xg for 1 hour. Pellets were resuspended in 0.01 M HEPES (N-2 hydroxyethyl piperazine-N'-2 ethane sulfonic acid) buffer, pH 7.4, at an approximate protein concentration of 20 mg/ml. The protein solutions were layered on a 35–55% (W/V) sucrose gradient prepared in 0.01 M HEPES buffer and OMP were pelleted by centrifugation at 131,000 xg for thirty-six hours. The OMP were resuspended in 0.01 M HEPES buffer containing 1 Mm $MgCl_2$ and sedimented by centrifugation (200,000 xg for 1 hour). Pellets were resuspended in the same buffer and stored at $-20°$ C. Protein concentrations were measured according to the procedure described above.

Immunoblotting: OMP (50 ug) and purified VT-1 and VT-2 (3–5 ug) were separated into individual protein bands by sodium dodecyl sulfate (SDS)—polyacrylamide gel electrophoresis. The gels were run in a double slab electrophoresis cell (Protean, Bio-Rad Laboratories, Richmond, Calif.) at a constant voltage of 200 V until bromophenol dye reached 1 cm from the bottom of the gel. After electrophoresis, protein bands were transferred to a PVDF membrane (Immobilim#, Millipore, Bedford, Mass.) in a buffer containing 25, mM Tris, 192 mM glycine and 20% methanol (W/V) using a transblot apparatus (Bio-Rad Laboratories, Richmond, Va.) at 30 V for 18 hours. The membrane was stained immunochemically as follows. Nonspecific binding sites were blocked by incubation with 5% BSA in TBS for 1 hour at 37° C. After rinsing the gel with 1% BSA in TBS, the PVDF membrane was incubated with monoclonal antibody 4E8C12 (Ascites fluid diluted 1:6000 in TBS) for 1 hour at 37° C. The membrane was washed 3 times with TBS plus 0.05% Tween-20 (TBS-T) and was incubated with alkaline phosphatase-labeled goat-anti-mouse (IgG diluted 1:2000 in TBS) for 30 minutes at 37° C. The membrane was washed thoroughly with TBS-T [+0.05% SDS] and treated with BCIP/NBT phosphatase substrate (Kirkegaard & Perry Laboratories, Inc., Gaithersburg, Md.) to detect protein bands. Low molecular weight standards (Electrophoresis Calibration Kit, Pharmacia, Piscataway, N.J.) were run on each gel and each was stained with 0.25% Commassie brilliant blue R-250 (Imperial Chemical, London) before and after transfer, to document the transfer of proteins.

EXAMPLE II

Determination of Sensitivity of the Monoclonal Antibody

The sensitivity of the monoclonal antibody was determined using a direct ELISA with various levels of 8 different strains of E. coli 0157:H7. The detection limit was in the range of $10^4$ to $10^5$ cells/ml. An example is shown in FIG. 1 which illustrates the sensitivity of monoclonal antibody 4E8C12 in a direct ELISA for detecting E. coli 0157:H7, strain 932.

EXAMPLE III

Specificity of the Monoclonal Antibody

The specificity of the monoclonal antibody was determined by examining the cross-reactivity with different enteric bacteria. The following bacteria listed in Table 1 of Example I were tested according to the procedures Example I. The results are presented below in Table 2.

TABLE 2

Reactivity of MAb 4E8C12 with E. coli 0157:H7 and Other Enteric Bacteria

| Organism | No. of Strains Tested | No. Positive[a] |
|---|---|---|
| Escherichia coli | | |
| 0157:H7 | 36 | 36 |
| 0157:H16 | 1 | 0 |
| 0157:H19 | 1 | 0 |
| 0157:H25 | 1 | 0 |
| 0157:H45 | 1 | 0 |
| 0157:H− | 1 | 0 |
| 02:K1:H7 | 1 | 0 |
| 026:H11[b] | 5 | 5 |
| 028ac | 1 | 0 |
| 0111 | 3 | 0 |
| 0113 | 1 | 0 |
| 0124 | 1 | 0 |
| 0128 | 1 | 0 |
| Additional serotypes other than 0157:H7 or 026:H11 | 23 | 0 |
| Escherichia hermanii | 1 | 0 |
| Proteus spp. | 3 | 0 |
| Klebsiella pneumoniae | 13 | 0 |
| Klebsiella oxytoca | 1 | 0 |
| Cytrobacter spp. | 11 | 0 |
| Serratia marcescens | 1 | 0 |
| Shigella dysenteriae | 2 | 0 |
| Salmonella spp. | 17 | 0 |

TABLE 2-continued

Reactivity of MAb 4E8C12 with E. coli 0157:H7 and Other Enteric Bacteria

| Organism | No. of Strains Tested | No. Positive[a] |
|---|---|---|
| Campylobacter jejuni | 5 | 0 |
| Yersinia enterocolitica | 12 | 0 |
| Enterobacter cloacae | 2 | 0 |
| Hafnia alvei | 1 | 0 |
| Aeromonas hydrophila | 4 | 0 |

[a]$OD_{410}$ value of 0.2 above background was considered positive; all positive strains had OD values >1.0 above background.
[b]E. coli 026:H11 were isolated from patients with hemolytic uremic syndrome or hemorrhagic colitis.

Discussion of Results: The MAb was highly reactive with all 36 strains of E. coli 0157:H7 as determined by ELISA, with an O.D. of >1.0 for all strains tested. The specificity of Mab 4E8C12 was determined by ELISA using E. coli strains other than serotype 0157:H7 and several strains of Y. enterocolitica, Salmonella spp., Enterobacter cloacae, C. jejuni, S. dysenteriae, Proteus spp., A. hydrophila, Hafnia alvei, K. pneumoniae, K. oxytoca, S. marcescens and Citrobacter spp. Five strains other than serotype 0157:H7, i.e., all E. coli 026:H11, reacted With the Mab (Table 1). These strains were isolated from patients with hemolytic uremic syndrome or hemorrhagic colitis and produce verotoxin identical to that produced by E. coli 0157:H7.

From the examples disclosed, one skilled in the art will appreciate that the monoclonal antibody disclosed above may be utilized in a variety of ways with respect to the antigen for which it has been shown to be specific. Thus, it may be used to assay E. coli 0157:H7 and 026:H11 in other ELISAs than sandwich ELISAs of the sort disclosed. It may be used as well in other conventional methods for utilizing an antibody for assay and other purposes, whether by utilization of immunofluorescence, immunoperoxidase reactions, or other such techniques.

Thus, it is understood that the present invention is not limited to the particular reagents, steps or methods disclosed herein. Instead it embraces all such modified forms thereof as come within the scope of the following claims.

What is claimed is:

1. The monoclonal antibody prepared from the hybridoma ATCC HB 10452.

2. The monoclonal antibody of claim 1 further characterized as binding to the strains of E. coli 0157:H7 and E. coli 026:H11 listed in Table 1 of the specification.

3. The monoclonal antibody of claim 1, which is specific to E. coli 0157:H7 and E. coli 026:H11, said monoclonal antibody being characterized in that it reacts with a protein having a molecular weight of approximately 13,000 daltons and being located in the other membrane of the cell wall of E. coli 0157:H7 or E. coli 026:H11.

4. The monoclonal antibody of claim 3 further characterized in that it is a member of the subclass immunoglobulin $G_{2a}$.

5. The monoclonal antibody according to claim 3 further characterized in that is has a kappa light chain.

6. The hybridoma ATCC 10452.

7. A continuous cell line which produces monoclonal antibodies prepared from hybridoma ATCC HB 10452 and specific to E. coli 0157:H7 and E. coli 026:H11, comprising:

(a) a fusing cell which specifically produces antibodies against E. coli 0157:H7 and E. coli 026:H11; and
(b) a myeloma cell.

* * * * *